(12) United States Patent
Shan et al.

(10) Patent No.: US 7,963,040 B2
(45) Date of Patent: Jun. 21, 2011

(54) SLITTER TOOL FOR CUTTING A TUBULAR SHEATH OF A GUIDE CATHETER

(75) Inventors: Nicolas Shan, Vincennes (FR); Jean-Francois Ollivier, Villiers le Bacle (FR)

(73) Assignee: Ela Medical S.A.S., Montrouge (FR)

( * ) Notice: Subject to any disclaimer, the term of this patent is extended or adjusted under 35 U.S.C. 154(b) by 453 days.

(21) Appl. No.: 12/233,197

(22) Filed: Sep. 18, 2008

(65) Prior Publication Data

US 2009/0071012 A1 Mar. 19, 2009

(30) Foreign Application Priority Data

Sep. 18, 2007 (FR) ..................................... 07 06550

(51) Int. Cl.
*A61B 17/32* (2006.01)
*A61M 25/00* (2006.01)
(52) U.S. Cl. ..................... 30/90.1; 604/164.05; 606/167
(58) Field of Classification Search .................... 30/280, 30/294, 90.1, 90.4, 90.8, 340; 604/161, 164.05; D24/144, 146, 147; 16/430; 606/167
See application file for complete search history.

(56) References Cited

U.S. PATENT DOCUMENTS

| | | | |
|---|---|---|---|
| 4,687,469 A | 8/1987 | Osypka | |
| 4,997,424 A | 3/1991 | Little | |
| 5,188,606 A | 2/1993 | Maloney et al. | |
| 5,330,460 A | 7/1994 | Moss et al. | |
| 6,159,198 A | 12/2000 | Gardeski et al. | |
| 6,497,681 B1 | 12/2002 | Brenner | |
| 6,625,496 B1 | 9/2003 | Ollivier | |
| 7,029,460 B2 | 4/2006 | Gardeski et al. | |
| D576,279 S * | 9/2008 | Bullemer et al. | ............ D24/147 |
| D576,280 S * | 9/2008 | Bullemer et al. | ............ D24/147 |
| 2005/0182435 A1 | 8/2005 | Andrews et al. | |
| 2006/0167417 A1 | 7/2006 | Kratz et al. | |
| 2007/0079511 A1* | 4/2007 | Osypka | .......................... 30/90.1 |
| 2007/0175049 A1* | 8/2007 | Goode et al. | .................... 30/280 |
| 2009/0054840 A1* | 2/2009 | Drake et al. | .................. 604/161 |

FOREIGN PATENT DOCUMENTS

EP 0391544 10/1990
EP 1155710 11/2001

* cited by examiner

*Primary Examiner* — Stephen Choi
(74) *Attorney, Agent, or Firm* — Orrick Herrington & Sutcliffe, LLP

(57) ABSTRACT

A tool for cutting or slitting the tubular sheath of a guide-catheter in the presence of a lead placed in this sheath. The tool (10) has a flattened, substantially planar blade holder body (12) with a cutting area (14) and a prehension area (16). The cutting area has a blade (18) and a tubular guide (22) receiving the lead for isolating it from the guide-catheter. The prehension area (16) has on a first side (30) an area for receiving the thumb and a lead holding pathway (68) spreading in the continuation of the tubular guide following an overall orientation forming an angle with this guide. The thumb reception area has a concave footprint (34) crossed through and through by the lead holding pathway (68), which spreads in the prehension area following an "S" shaped curve having a first curved area (74) and a second counter-curved area (76). The minimal distance between the blade (18) and the contour of the first footprint (34) is to the most equal to 15-20 mm.

17 Claims, 3 Drawing Sheets

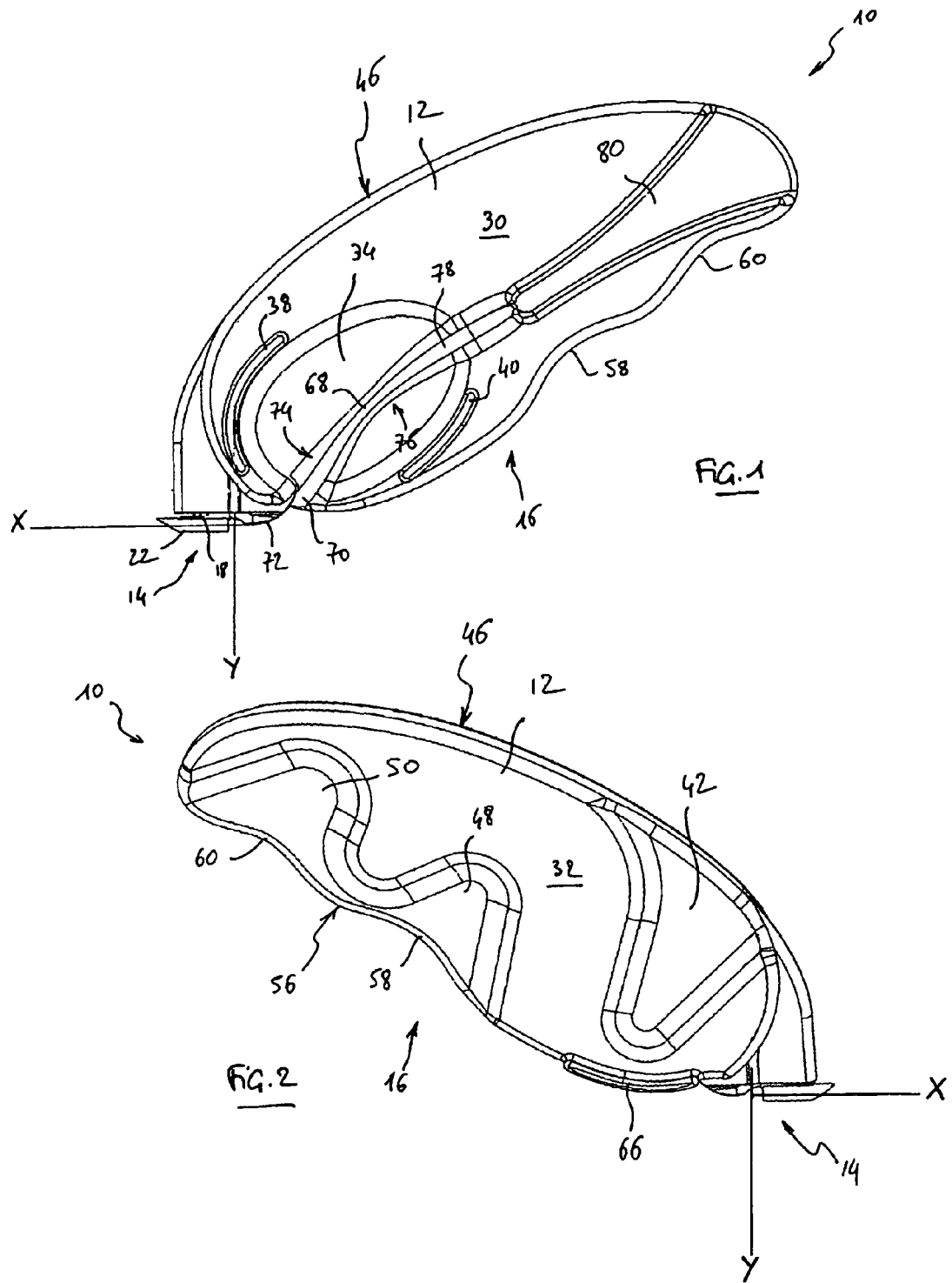

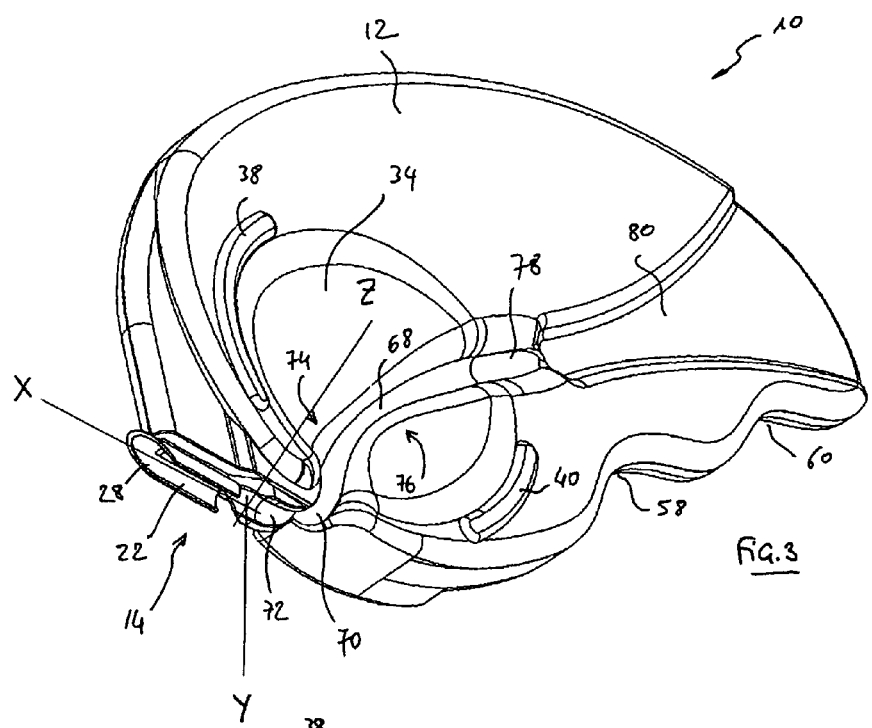
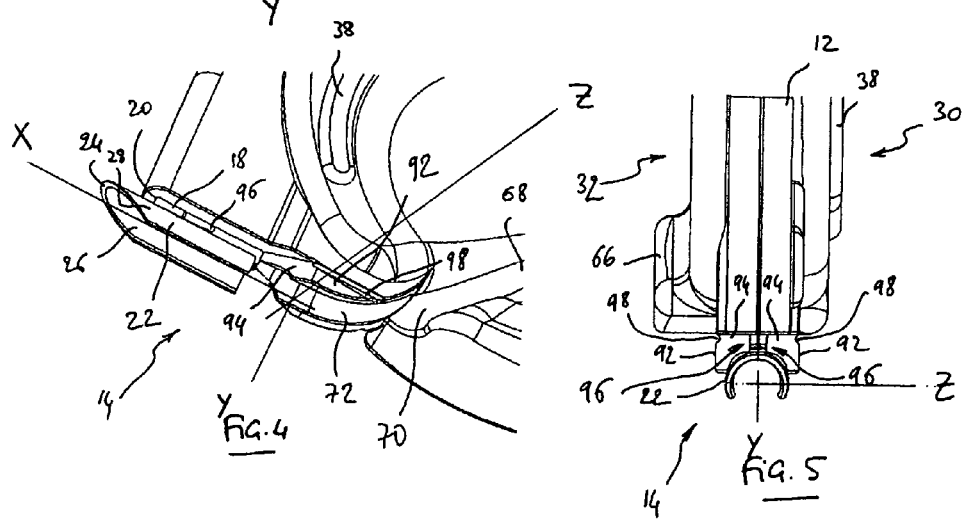
FIG. 3
FIG. 4
FIG. 5

SLITTER TOOL FOR CUTTING A TUBULAR SHEATH OF A GUIDE CATHETER

FIELD OF THE INVENTION

The present invention is related to the implantation of intracorporal leads, more particularly leads for cardiac sensing/pacing that are usually associated with "active implantable medical devices" as such devices are defined by the Jun. 20, 1990 directive of the Counsel of European communities, and more specifically to implantable devices for cardiac pacing, resynchronization, cardioversion and/or defibrillation.

BACKGROUND OF THE INVENTION

Cardiac leads may be endocardial leads, such as leads for sensing/pacing in right heart cavities, or leads introduced in the coronary network, notably leads comprising an electrode positioned in front of a left cavity of the myocardium.

The insertion of the latter type of leads, carried out through endocavitary approaches, is a particularly tricky intervention, taking into account the difficult access to the coronary sinus entrance via the right atrium, and also the required accuracy for the pacing sites once the lead is guided to its desired position and immobilized within the coronary network.

One of the implantation techniques of such a lead requires an accessory known as "guide-catheter". This accessory comprises a hollow tubular sheath reinforced by a wire mesh and with an inner surface presenting a low coefficient of friction (for example, a surface made with PTFE, extruded or co-molded with the rest of the sheath). In addition, the sheath is designed to present a flexibility allowing a stiffness in torsion high enough to allow transmission of a rotation movement from one end to the other, so as to allow guiding the lead tip within the myocardium during the procedure.

Once in place, the guide-catheter serves as a direct "tunnel" between the "external world" and the coronary sinus, a tunnel that can be utilized by the surgeon for sliding the lead through up to its final target site.

Once the lead is in place, the guide-catheter needs to be extracted, and the extraction procedure is tricky because the lead must not be displaced, or its position or orientation altered as a result of the extraction.

These catheters also need to have a minimum diameter so as to allow their navigating through blood vessels while being less traumatic and more easily guidable. Also, the catheter dimensions are adjusted to the lead for a better performance.

One other difficulty of this extraction step is due to the presence of the electrical connector, at the proximal end of the lead. The diameter of this connector is greater than that of the internal lumen of the guide-catheter, and it prevents the guide-catheter from being withdrawn by being simply slid backwardly along the lead.

The step of extracting the guide-catheter therefore usually requires it to be cut, starting from its proximal end and along a generatrix line by means of a slitting tool, also known as "slitter", for slitting the proximal end of the catheter and reinforcement wire mesh forming the frame of the hollow sheath.

With one hand, the surgeon then pulls the guide catheter towards him with a continuous gesture, while firmly maintaining the lead and the slitting tool with the other hand, allowing the slitting tool to simultaneously slit the sheath as it is being thus extracted.

It has already been proposed in the prior art, in order to avoid resorting to a sharp cutting tool, to use a non-reinforced sheath that is simply strippable. However, cutting of such a sheath along its whole length leads to a weakness and a lower rigidity of the guide-catheter, with a risk of folding and lower transmission of efforts (applied forces) during its setting up preparatory to an intervention event. It has also been proposed, notably by European patent EP 1,155,710 and its U.S. counterpart U.S. Pat. No. 6,625,496 (commonly assigned herewith to ELA Medical), to provide the lead with a removable connector, which avoids having to cut the guide-catheter. This method however leads to an increasing number of steps required for setting up and assembling the different elements, and also renders the intervention procedure more complicated.

Therefore, slitting/cutting of the guide-catheter is, in practice, the most usual way to proceed.

One of the main difficulties inherent to this method, lies in the risk of a lead displacement during the catheter extraction. In such case, it is necessary to completely remove the lead and start over again, from the very beginning, the procedure of insertion and placement of the lead. This implies a significantly longer intervention time, particularly with left ventricular leads, which take a very long time to implant anyway, and additional risks associated with the prolongation of an already very long intervention.

Some slitting tool configurations have for example been proposed in U.S. Pat. Nos. 4,687,469 (Osypka), 4,997,424 (Little), 6,159,198 (Gardeski), 5,330,460 (Moss) and 7,029,460 (Gardeski). The devices described in these patents propose various ways of maintaining the lead during the procedure of cutting the guide-catheter, and protecting the lead from being damaged by the blade during this operation.

U.S. patent application 2007/0079511, describes a cutting tool having a blade holder with a flattened shape to be held between two fingers (thumb and forefinger). This blade holder comprises, in its rear area, a footprint for the thumb, which is crossed by a curved pathway located in the continuation of a tubular element receiving and guiding the lead in the vicinity of the blade during the cutting of the guide-catheter sheath.

In concrete terms, the devices heretofore proposed in the prior art all present certain drawbacks.

In particular, the risk referred to above, which is a large risk, of a lead displacement during the cutting operation, is increased by the fact that the lead is not maintained in the critical area of cutting of the catheter, an area where the constraint during the operation, is focused. For that reason, there is a remaining risk of a displacement of the lead relative to the catheter, with the formation of a "loop" level with the maintaining area, leading to a high risk of displacement of the opposite end (distal end) located level with the implantation site, such a displacement requiring a complete starting over of the procedure.

Also, with the slitting tools that have been proposed so far, the prehension of the tool is ensured by a pinching between the thumb and forefinger, with a risk of instability during handling that is as much high as the required cutting force is high, notably in the case of relatively thick and strongly reinforced guide-catheters.

As for the prehension of the lead, it is equally ensured by the fingers, but at a relatively large distance from the area where the cutting of the guide-catheter is effectively realized, which reduces the stability of the whole assembly set up during the operation.

To summarize, the slitting tools that have been proposed so far always require a very accurate dexterity and a great experience of the surgeon so as to avoid any mishandling that would be disastrous.

OBJECTS AND SUMMARY OF THE INVENTION

It is an object of the present invention to palliate all these difficulties, by proposing a cutting tool of the slitter type which, from an ergonomic point of view, is better than what has been proposed up to know, and allows a simple and safe handling by the surgeon.

To that purpose, the present invention proposes an improvement of the slitting tool of the general type as described in the aforementioned US 2007/0079511. Broadly, the invention is directed to a slitting tool for cutting a tubular sheath of a guide-catheter along a generatrix of said sheath in the presence of a lead placed in an internal lumen of this sheath. One aspect of the slitting tool invention is directed toward a slitting tool comprising a blade holder body having a roughly flattened shape, generally or substantially planar, that is able to be held between the fingers of a user, wherein the blade holder body includes:
a cutting area with:
  a blade presenting a cutting edge roughly lying in the median plane of the blade holder body, the cutting edge being directed toward the outside of the blade holder body following a cutting direction (X) corresponding to said generatrix of the sheath to be cut, and
  a straight tubular guide, roughly parallel to the cutting direction, said tubular guide being able to receive the lead at an open side, opposite to the blade, and being able to receive the guide-catheter at the blade side,
a prehension area continuing the cutting area level with the rear of said cutting area, with:
  on a first side of the blade holder body, an area for receiving the thumb of the user, comprising a first concave footprint or hollow formed in the first side of the blade holder body and
  on a second side, opposite to said first side, an area for receiving the forefinger of the user, and
  a holding pathway for the lead, spreading in the prehension area following a way comprising at least a curved area crossing through and through the first footprint and in the continuation of the tubular guide and following an overall orientation presenting an angle with said tubular guide,
wherein said tool is further characterized by:
  the minimal distance between the blade and the contour of said first footprint being less than or equal to 20 mm, and
  the lead holding pathway is spreading in the prehension area following a "S" way comprising at least a curved area and a counter-curved area.

Various additional advantageous characteristics include the following. Preferably, the minimal distance between the blade and the contour of the first footprint less than or equal to 15 mm.

In one embodiment the edge of the blade holder body presents, in the area opposite to the blade, a profile conformed to the curve of the palm of a hand. In an alternative embodiment, the edge of the blade holder body presents, in the area opposite to the profile conformed to the palm of a hand, a profile with at least one indentation for receiving the phalanges of the hand. Optionally, the second side of the blade holder body comprises at least a third concave footprint for the reception of a distal phalanx of the hand.

Yet another embodiment provides that the area for receiving the forefinger comprises a second concave footprint, formed in the second side of the blade holder body.

Advantageously, the tool includes stop reliefs for the thumb, formed on the contour of the first concave footprint, on both sides of said lead holding pathway. It also may include a stop relief for the forefinger, formed on the second side of the blade holder body in the vicinity of the cutting area.

The lead holding pathway is preferably flared in its tip area spreading in the vicinity of the tubular guide. Further, the depth of said lead holding pathway is chosen, in the central area of the first concave footprint, to be less than the nominal diameter of the lead.

The blade holder body material preferably is made of a material presenting, in the area of the first footprint, a deformability that is higher than that of the material of the rest of the blade holder body.

The tubular guide preferably comprises an antifriction material, which may be a metal.

In one embodiment, the cutting area has, level with the rear of the blade, reliefs for separating the lips of the cut guide-catheter, said separator reliefs being placed at both sides, and at the rear of said tubular guide. More preferably, the separator reliefs are each have respective grooves for guiding the lips of the cut guide-catheter, said leads being oriented generally parallel to the cutting direction (X). The guiding grooves are optionally placed at the front of the holding pathway, to provide a smooth guiding action of the cut guide-sheath away, and the guiding grooves also may extend into the holding pathway.

BRIEF DESCRIPTION OF THE DRAWINGS

Further features, advantages and characteristics of the present invention will become apparent to a person of ordinary skill in the art in view of the following detailed description of preferred embodiments of the invention, made with reference to the drawings annexed in which like reference characters refer to like elements, and in which:

FIGS. 1 and 2 are respectively front and back elevation views of a slitting tool of a preferred embodiment of the present invention;

FIG. 3 is a perspective view, three-quarter from below, of the slitting tool of FIGS. 1 and 2;

FIG. 4 is a detail of FIG. 3, more precisely showing the various elements constituting the cutting area;

FIG. 5 is a side elevation of the detail showed in FIG. 4;

DETAILED DESCRIPTION OF THE INVENTION

Figure 6:
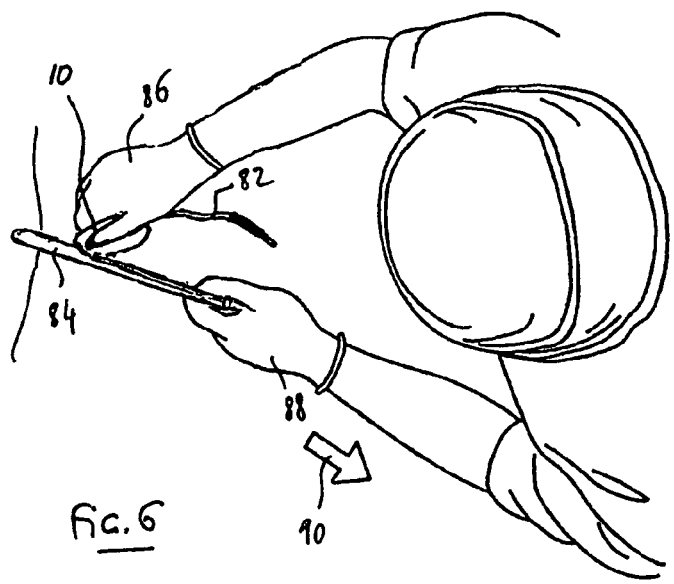
FIG. 6 schematically represents the extraction and cutting of the guide-catheter by a surgeon using a slitting in accordance with the present invention.

One will now describe an embodiment of the slitter tool according to a preferred embodiment of the present invention. With reference to the figures, reference 10 generally corresponds to the slitting tool or "slitter" tool of the present invention. Tool 10 comprises a blade holder body 12 with a roughly flattened shape, comprising a cutting area 14 and a prehension area 16.

Tool 10, for example, presents the following typical overall dimensions: length (the longer longitudinal dimension of the tool) of 65 to 100 mm, width (the longer transversal dimension) of 35 to 40 mm, and thickness of 5 to 6 mm. Of course, these dimensions are exemplary, and in no way limitative; and one of ordinary skill in the art will understand that the size of tool 10 must be such that the tool may be handled in the inside of a surgeon's hand, and not merely between the thumb and the forefinger, as it is the case with the various slitter tools that have been proposed by the prior art so far.

Cutting area 14 comprises (see, e.g., FIG. 4) a blade 18 having a cutting edge 20 that is turned toward a direction X, hereafter referred to as the "cutting direction", corresponding to the generatrix of the incision to be formed in the sheath of the guide-catheter to be extracted. The other directions are the lateral direction Y, perpendicular to the cutting direction X and located in the plane of the flattened blade holder body 12, and the vertical direction Z, perpendicular to the plane of the blade holder body (the latter being therefore within the plane XY).

Also foreseen in the cutting area 14 is a straight tubular guide 22 having a wall 24 that is open downward, i.e., in the direction Y. The tubular guide 22 defines a cylindrical interior volume 26 whose inner diameter corresponds to the outer diameter of the lead, so as to fit it and protect it against the blade 20. As to the guide-catheter, it will come and slide on the external surface 28 of tubular guide 22. In other words, the tubular guide 22 will come and interpose between the lead (to be protected) and the guide-catheter (to be cut).

In the prehension area 16, blade holder body 12 has a first side 30, shown in FIG. 1, and a second side 32, opposite to the first, as shown in FIG. 2.

Figure 7:
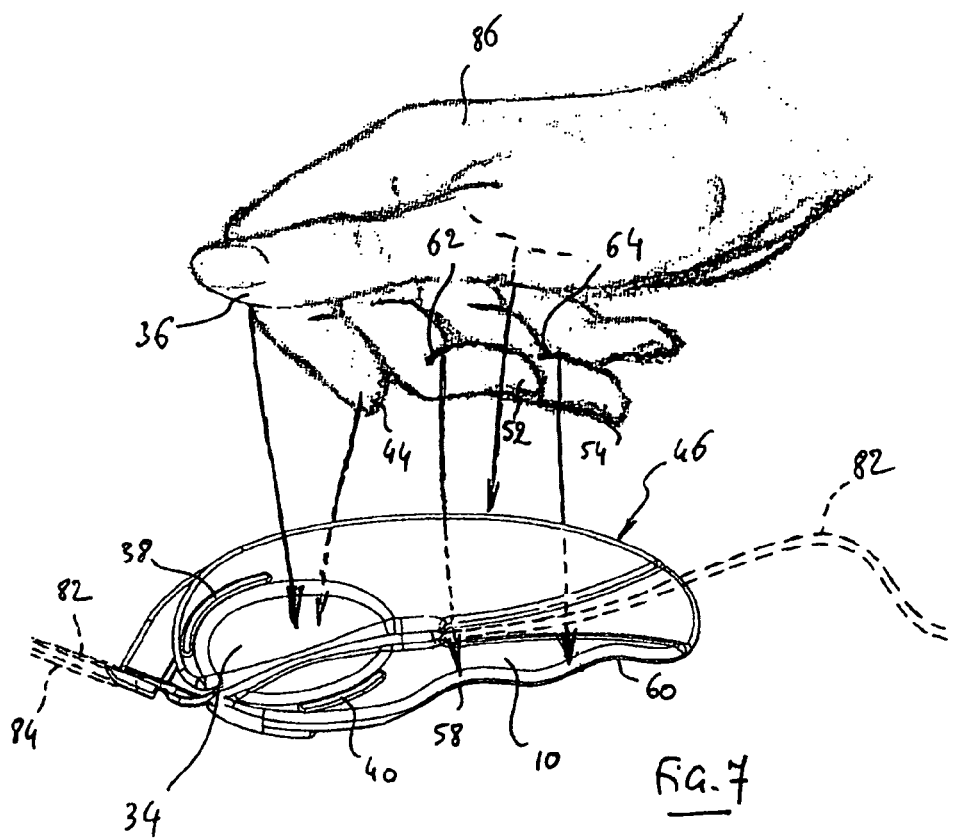
FIG. 7 shows the ergonomics of a tool of FIGS. 1 and 2 illustrating the way its shape is adapted to the morphology of the hand.

The side 30 comprises a hollow or concave footprint 34 that is preferably conformed and dimensioned so as to receive the thumb 36 of the surgeon (see FIG. 7). In a preferred embodiment of this invention, this concave footprint 34 is provided with opposite stop reliefs 38, 40 allowing to prevent from the thumb sliding out of the cavity 34 during the procedure.

In a further preferred embodiment of the invention, the minimum distance between blade 18 of the cutting area 14 and concave footprint 34 of the prehension area 16 is reduced to a dimension that is less than or equal to 20 mm, and more preferably less than 15 mm maximum, so as to maximize the stability of the whole tool 10 during the cutting procedure.

Also, in a further preferred embodiment of the present invention, the area of concave footprint 34 is made of a material that is different from that of the rest of the blade holder body 12. The material in the concave footprint 34 is preferably a more flexible material, for example, an elastomer material co-molded with the rest of the blade holder body 12, than the rest of the blade holder body 12 which is more rigid (preferably for a better setting of the blade). This better deformability, compared to that of the material of the rest of the blade holder body, improves the friction and conforming of the material over the lead.

The second side 32 of the blade holder body (see FIG. 2) comprises a hollow or concave footprint 42 for receiving the forefinger 44 (see FIG. 7), and its superior edge 46 presents a rounded profile dimensioned and adapted so as to fit the inside of the hand with as good as possible holding and comfort.

The second side 32 also comprises two additional concave footprints 48, 50 for the distal phalanges of the forefinger 52 and ring finger 54 respectively. As for the inferior profile 56, it is conformed with two indentations 58, 60 for respectively receiving the joints 62, 64 between middle and distal phalanges of the forefinger and ring finger.

Finally, it is foreseen, in the continuation of concave footprint 42, in the vicinity of cutting area 14, a stop relief 66 allowing to protect the tip of the surgeon's forefinger during the cutting procedure.

Such conformation described above allows a superior holding of the tool 10 by the surgeon, thanks to its large handling and the way it shall be hold, which allows to withstand the various stresses, relatively high, level with the blade during cutting and extraction of the guide-catheter.

One will now describe a way the tool 10 is conformed so as to receive and hold the lead in a preferred efficient manner during this procedure. To that purpose is the concave footprint 34 traversed by a groove or lead holding pathway 68, through and through the longer dimension of this footprint. One of the ends 70 of the lead holding pathway 68 is located in the vicinity of the cutting area 14, and at this location it is foreseen, in order to ensure a continuation with tubular guide 22, a transition part 72 of curved and rounded shape (see FIG. 4) allowing to hold the lead in an almost continuous way from the tubular guide 22, via element 72, to the holding pathway 68.

The holding pathway 68, crossing the concave footprint 34, is within the plane XY, which is also that of the blade holder body, following a general direction forming an angle with the cutting direction X, thus defining a first curving area 74, continued by the rounded shape of element 72.

In a preferred embodiment of the invention, the holding pathway 68 presents, in the area of concave footprint 34, an "S" shape, i.e., the curve 74 is continued by a counter-curve 76 toward the end 78, opposite to the end 70 that is in the vicinity of cutting area 14. Finally, out from concave footprint 34, the holding pathway 68 is continued by a flare 80, corresponding to an area where the lead presents no, or few, risks of being stressed mechanically. The opposite area 70 is also slightly flared, so as to ease the placement of the lead in the holding pathway.

The depth (toward Z direction) of holding pathway 68 in the area of footprint 34 is, in a preferred embodiment of the invention, is slightly less than the lead diameter. Thus, at the centre of footprint 34, in the area where the gripping force of the thumb is the highest, the lead can be compressed directly by the thumb, thus ensuring a maximal holding of the lead on the slitting tool.

It should be understood by a person of ordinary skill in the art that the particular geometry as described above provides a particularly effective lock of the lead, insofar as the latter is being blocked in two perpendicular planes: in the plane XZ through tubular guide 22; then in the plane XY through the lead pathway 68. Such a configuration is favorable to blocking the lead, therefore to a better holding in place thereof, and reduction of the degrees of freedom.

The slitting tool of this invention is, in accordance with a preferred embodiment of the present invention, suitable for use in the following manner.

With reference to FIGS. 6 and 7, after placing the lead 82 in the tubular guide 22 and in pathway 68, the surgeon positions the tool blade 10 against the free end of guide-catheter 84. The tool 10 is held still by hand 86, with the lead being firmly secured thereto by means of the thumb of the same hand. With the other hand 88, the surgeon then extracts the guide-catheter 84 by pulling it backward (arrow 90), until there is a complete extraction.

In a preferred embodiment of the invention, the surface of tubular guide 22 comprises an antifriction material, for example, a metal coating. This improves sliding of the lead in this compression area. Indeed, during the cutting motion, the lead is strongly compressed by friction with the catheter, and this compression increases the friction that is accumulated right in front of the slitting tool blade. If the lead is surrounded by an antifriction material upstream of the cutting area, then the friction in this area can be reduced, which facilitates the cutting procedure, particularly if the tubular guide 22 is noticeably prominent upstream of the blade 18 along the cutting direction X.

During the extraction procedure, it should be understood that the catheter is slit along a generatrix, in such a way that along the incision, two lips whose edge can be damageable subsist, notably due to the cut reinforcement wire mesh of the catheter. In order to prevent these lips from damaging the lead during the extraction, is foreseen in the cutting area 14, at each end of the transition element 72 of the lead pathway 68, to provide separate reliefs 92, each linked through a ramp 94 to the area 96, which is located right at the rear of blade 18. The two lips of the catheter thus can be separated one from the other in the area where the lead is no longer protected by the tubular guide 22. In addition, guiding grooves 98 are disposed on opposite sides of the cutting area so that the cut guide-sheath that is advanced along ramp 94 during the cutting action is then guided by the grooves away so as to avoid any sliding of the catheter lips in the critical area where it is necessary to protect the lead from any contact therewith.

In the figures, these guiding grooves are represented at a position before the holding pathway 68, but they can equally be positioned behind this pathway, so as to ensure a longer guiding of the cut lips of the catheter, especially on both sides of the area where the lead and catheter are separating from each other. For example, grooves 98 can extend along a line in the same direction a parallel to the cutting edge in direction X, and eventually end either at or further backward of the end of the region corresponding to reference 70. Other configurations are within the abilities of a person of ordinary skill in the art to configure the length and orientation of the guiding grooves.

The tool in accordance with the present invention presents many major advantages compared to the prior art.

Thus, by providing the lead with a sinuous "S" shape in the holding area, the risks of sliding between the tool and the lead are dramatically reduced, the lead being "locked" in place through the pressure by the thumb in corresponding footprint.

In addition, with the lead being guided along almost its whole length between the cutting point and the point where it is blocked in the cavity, the risk for a displacement is very low. Also, due to the close proximity between the contour of the footprint receiving the thumb, and the blade, the risk of forming a loop and therefore displacing the lead tip, is extremely reduced.

It also should be understood that the force exerted by the thumb on the tool 10, and therefore on the lead, is following direction Z, perpendicular to the plane XY of the tool and therefore to the cutting direction X. The catheter extraction—following this direction X—will not induce any disturbing component along the perpendicular direction Z, and will therefore not affect the pressure exerted by the surgeon for holding the lead.

Finally, the fact that the tool is dimensioned so as to be held in the inside of the hand, and not simply pinched between the thumb and forefinger, provides much better ergonomics, which considerably improves the stability of holding the lead, and the cutting accuracy during the extraction of the guide-catheter.

One skilled in the art will appreciate that the present invention can be practiced by other than the described embodiments and particular values referenced for the various operating constructions, which are presented for purposes of illustration and not of limitation.

We claim:

1. A tool for cutting a tubular sheath of a guide-catheter along a generatrix of said sheath in the presence of a lead placed in an internal lumen of this sheath, said tool comprising
    a blade holder body having a roughly flattened shape able to be held between the fingers of a user and a median plane, said blade holder comprising:
        a cutting area, and
        a blade presenting a cutting edge roughly lying in the median plane of the blade holder body,
    wherein said cutting edge is directed toward the outside of the blade holder body following a cutting direction (X) corresponding to said generatrix of the sheath to be cut, and
        a straight tubular guide, roughly parallel to the cutting direction, said tubular guide being able to receive the lead at an open side, opposite to the blade, and being able to receive the guide-catheter at the blade side,
        a prehension area adjacent the cutting area and level with the rear of said cutting area, the prehension area having a first side and a second side opposite the first side, the first side further comprising a first concave footprint formed for receiving the thumb of the user, and the second side further comprising an area for receiving the forefinger of the user, and
        a holding pathway for the lead disposed in the prehension area, said holding pathway comprising at least a curved area crossing through and through the first footprint and in the continuation of the tubular guide and following an overall orientation presenting an angle with said tubular guide,
    wherein said tool is further characterized by:
        the minimal distance between the blade and the contour of said first footprint being less than or equal to 20 mm, and
        the lead holding pathway in the prehension area further comprises an "S" shaped pathway comprising at least a first curved area and a second counter-curved area.

2. The tool of claim 1, further comprising a minimal distance between the blade and the contour of the first footprint that is less than or equal to 15 mm.

3. The tool of claim 1, wherein the edge of the blade holder body further comprises, in an area opposite to the cutting blade, a first profile conformed to the curve of the palm of a hand.

4. The tool of claim 3, wherein the blade holder body edge further comprises, in an area opposite to said first profile, a second profile having at least one indentation for receiving a phalange of a hand.

5. The tool of claim 4, wherein said second side of the blade holder body further comprises at least a third concave footprint for the reception of a distal phalanx of the hand.

6. The tool of claim 1, wherein the area for receiving the forefinger comprises a second concave footprint, formed in the second side of the blade holder body.

7. The tool of claim 1, further comprising at least one stop relief for a thumb, positioned along the contour of the first concave footprint, on both sides of said lead holding pathway.

8. The tool of claim 1, further comprising a stop relief for the forefinger, formed on the second side of the blade holder body in the vicinity of the cutting area.

9. The tool of claim 1, wherein the width of said lead holding pathway is flared in its tip area spreading in the vicinity of the tubular guide.

10. The tool of claim 1, wherein said lead holding pathway has a depth chosen, in the central area of the first concave footprint, to be less than a nominal diameter of the lead.

11. The tool of claim 1, wherein the blade holder body material further comprises a material having, in the area of the first footprint, a deformability higher than that of the material of the rest of the blade holder body.

12. The tool of claim 1, wherein the surface of the tubular guide further comprises an antifriction material.

13. The tool of claim 12 wherein the antifriction material further comprises a metal.

14. The tool of claim 1, wherein the cutting area further comprises, level with the rear of the blade, at least two reliefs for separating the lips of the cut guide-catheter, said separator reliefs being placed at both sides, and at the rear of said tubular guide.

15. The tool of claim 14, wherein said at least two separator reliefs further comprise corresponding grooves for guiding the lips of the cut guide-catheter, said guiding grooves being generally oriented in parallel to the cutting direction (X).

16. The tool of claim 15, wherein said guiding grooves are disposed adjacent the holding pathway and on opposite sides of said cutting area.

17. The tool of claim 16 wherein said guiding grooves each has a length that extends to about the end of the holding pathway.

* * * * *